United States Patent [19]

Hoshi et al.

[11] Patent Number: 4,619,925

[45] Date of Patent: Oct. 28, 1986

[54] 3-PROPENYL CEPHALOSPORIN DERIVATIVES

[75] Inventors: Hideaki Hoshi, Chiba; Takayuki Naito, Kawasaki, both of Japan

[73] Assignee: Bristol-Myers Company, New York, N.Y.

[21] Appl. No.: 796,146

[22] Filed: Nov. 8, 1985

[51] Int. Cl.[4] .................. C07D 501/22; A61K 31/545
[52] U.S. Cl. ..................................... 514/200; 540/215; 544/209
[58] Field of Search .................. 544/16; 514/200, 209

[56] References Cited

U.S. PATENT DOCUMENTS 4,520,022  5/1985  Hoshi et al. ........................ 544/16

Primary Examiner—Nicholas S. Rizzo
Attorney, Agent, or Firm—Robert E. Carnahan

[57] ABSTRACT

The present invention relates to 7-[(D)-2-amino-2-(3-hydroxyphenyl)acetamido]-3-[(Z)-1-propenyl]-3-cephem-4-carboxylic acid, which is an orally active antibiotic against Gram-positive and Gram-negative bacteria.

4 Claims, No Drawings

3-PROPENYL CEPHALOSPORIN DERIVATIVES

DESCRIPTION OF THE PRIOR ART

U.S. Pat. No. 4,520,022, issued May 28, 1985 to Hoshi et al., discloses compounds of the formula

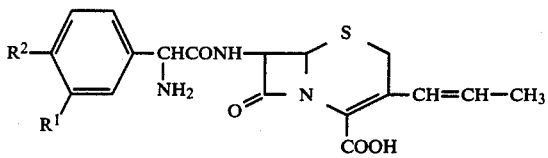

wherein the 3-propenyl group has the Z-configuration, $R^1$ is hydrogen, chlorine or methoxy, and $R^2$ is hydrogen or hydroxy with the proviso that when $R^2$ is hydrogen, $R^1$ is also hydrogen. One of the representative compounds disclosed therein is 7-[D-2-amino-2-(4-hydroxyphenyl)acetamido]-3-[(Z)-1-propen-1-yl]-3-cephem-4-carboxylic acid of the following formula referred to as BMY-28100.

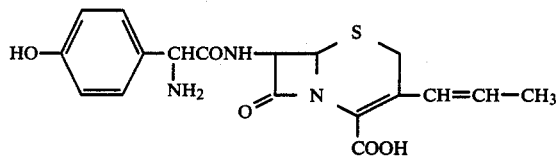

SUMMARY OF THE INVENTION

The present invention provides the compound of Formula I, named 7-[(D)-2-amino-2-(3-hydroxyphenyl)acetamido]-3-[(Z)-1-propenyl]-3-cephem-4-carboxylic acid, also referred to as BMY-28272.

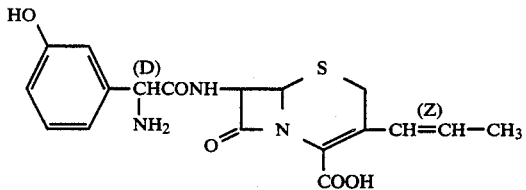

This compound is of interest as an orally effective cephalosporin antibiotic having strong activity against Gram-positive bacteria and an improved spectrum of activity against Gram-negative bacteria and fastidious bacteria relative to cephalexin and cefaclor. It provides prolonged antibiotic concentrations in the bloodstream following oral administration and is suitable for administration to humans on a once- or twice-a-day basis. As such, it is administered in doses ranging from 100 mg to 5000 mg per day, depending upon the size of the patient and the disease condition. It may be administered parenterally in similar dosage amounts. For this purpose, they are administered orally or parenterally in antibacterially effective non-toxic doses as such or in the form of one of its pharmaceutically acceptable acid addition salts, pharmaceutically acceptable metal or amine salts, or as a pharmaceutically acceptable ester.

The pharmaceutically acceptable acid addition salts are those in which the anion does not contribute significantly to the toxicity of the salt and which salts are compatible with the customary pharmaceutical vehicles and adpated for oral or parenteral administration. They include the salts with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, methanesulfonic acid, p-toluenesulfonic acid, and other acids known and used in the penicillin and cephalosporin arts. Preparation of these salts is carried out by conventional techniques involving reaction of the cephaolsporin I with the acid in a substantially equivalent amount.

Pharmaceutically acceptable metal and amine salts are those salts of the compound I in which the cation does not contribute significantly to the toxicity or biological activity of the salts. Suitable metal salts include the sodium, potassium, barium, zinc, and aluminum salts. The sodium or potassium salt is preferred. Amine salts prepared from amines used, for instance, with benzyl penicillin, which are capable of forming stable salts with the acidic carboxyl group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, and dicyclohexylamine.

Pharmaceutically acceptable esters include those esters which are active per se or which serve as prodrugs by being hydrolyzed in the body to yield the antibiotic per se. Suitable esters of the latter type are the phenacyl, acetoxymethyl, pivaloyloxymethyl, α-acetoxyethyl, α-acetoxybenzyl, α-pivaloyloxyethyl, 3-phthalidyl, 5-indanyl, methoxymethyl, benzoyloxymethyl, α-ethylbutyryloxymethyl, propionyloxymethyl, valeryloxymethyl, isobutryloxymethyl, glycyloxymethyl, and others known in the penicillin and cephalosporin arts.

The compound of Formula I may be formulated for oral or parenteral use in a conventional manner using known pharmaceutical carriers and excipients, and it may be presented in unit dose form or in multiple dose containers. The compositions may be in the form of tablets, capsules, solution, suspensions, or emulsions. This compound may also be formulated as suppositories utilizing conventional suppository bases such as cocoa butter or other fatty materials. The suppository may contain nonionic surfactants. The compound may, if desired, be administered in combination with other antibiotics including cephalosporins, penicillins, and aminoglycosides.

DETAILED DESCRIPTION OF THE INVENTION

Table 1 provides the in vitro activity of the cephalosporins BMY-28272, BMY-28100, cephalexin, and cefaclor. Minimum inhibitory concentrations (MIC's) determined by the agar dilution technique for four groups of organisms designated Gp-Ia, Gp-Ib, Gn-Ia, and Gn-Ib are provided. Each of these groups of organisms is constituted of five individual strains of microorganism. The Gp-Ia organisms are Gram-positive staphylococci which are sensitive to penicillin. The Gp-Ib organisms are Gram-positive staphylococci which are resistant to penicillin and produce penicillinase. The Gn-Ia organisms are Gram-negative bacteria which are sensitive to ampicillin and cephalothin. The Gb-Ib organisms are Gram-negative bacteria which are resistant to ampicillin and cephalothin. Against Gp-Ia organisms, BMY-28272 is two or four times more active than cephalexin and cefaclor, and same as BMY-28100. Against Gp-Ib strains, BMY-28272 is slightly less active than BMY-28100, while three times more active than cephalexin or cefaclor. Against Gn-Ia bacteria, both of the hydroxyphenyl derivatives, BMY-28272 and BMY-28100 are more active than cephalexin and slightly better than cefaclor. In the Gn-Ib area, none of these cephalosporins shows useful activity.

TABLE 1

Agar Dilution Technique (Mueller-Hinton Agar)
Minimum Inhibitory Concentration (mcg/ml)

R—CHCONH— [β-lactam structure] —CH=CH—CH₃
  |
  NH₂

R = (BMY-28272) hydroxyphenyl (meta-HO); HO-phenyl (para) = (BMY-28100)

| Organism | (BMY-28272) | (BMY-28100) | cepha-lexin | cefa-clor |
|---|---|---|---|---|
| [Gp-Ia] | | | | |
| S. aureus Smith | 0.4 | 0.4 | 1.6 | 0.8 |
| S. aureus A9497 | 0.4 | 0.4 | 1.6 | 0.8 |
| S. aureus Terajima | 0.4 | 0.4 | 1.6 | 0.4 |
| S. aureus A9534 | 0.4 | 0.4 | 1.6 | 0.8 |
| S. aureus A9601 | 0.8 | 0.8 | 1.6 | 1.6 |
| [Gp-Ib] | | | | |
| S. aureus No. 193 | 1.6 | 1.6 | 6.3 | 6.3 |
| S. aureus BX-1633-2 | 1.6 | 0.8 | 6.3 | 6.3 |
| S. aureus A15092 | 1.6 | 1.6 | 6.3 | 6.3 |
| S. aureus Russell | 1.6 | 0.8 | 3.1 | 3.1 |
| S. aureus A9602 | 0.8 | 0.8 | 3.1 | 3.1 |
| [Gn-Ia] | | | | |
| E. coli Juhl | 1.6 | 1.6 | 6.3 | 0.8 |
| E. coli A9660 | 0.8 | 0.8 | 6.3 | 0.8 |
| K. pneumoniae D11 | 0.8 | 0.8 | 6.3 | 0.8 |
| P. mirabilis A9554 | 0.8 | 0.8 | 12.5 | 1.6 |
| P. mirabilis A9900 | 0.8 | 0.8 | 12.5 | 1.6 |
| [Gn-Ib] | | | | |
| E. coli A15148 | 25 | 50 | 100 | 25 |
| E. coli A20341-1 | 12.5 | 25 | 6.3 | 6.3 |
| E coli RGN-823 | 50 | >50 | 12.5 | 25 |
| K. pneumoniae A20346 | 50 | 25 | 6.3 | 6.3 |
| K. pneumoniae A20345 | 6.3 | 6.3 | 6.3 | 1.6 |

Gp-Ia = penicillin sensitive (no penicillinase produced)
Gp-Ib = penicillin resistant (penicillinase producers)
Gn-Ia = ampicillin and cephalothin sensitive
Gn-Ib = ampicillin and cephalothin resistant The data in Table 2 are results of protective doses (PD$_{50}$) for mice infected with a lethal inoculum of bacteria. Two different bacteria were employed in the studies, one a Gram-positive organism (*S. aureus* Smith) and the other a Gram-negative organism (*E. coli* Juhl). The PD$_{50}$ is that dose which, when administered to a group of injected mice, results in 50% survival after five days. Normally untreated infected mice die within three days following injection of the lethal inoculum. The effectiveness of BMY-28272 in vivo is confirmed.

TABLE 2

Protective Dose for Mice Infected with Lethal Inoculum

| Compound | Route | S. aureus Smith | E. coli Juhl |
|---|---|---|---|
| BMY-28272 | po | 0.17 | 2.6 |
| | im | 0.29 | 1.9 |
| cefaclor | po | 0.20 | 1.1 |
| | im | — | 0.8 |

Table 3 contains comparative blood level data for mice treated orally and intramuscularly with the hydroxyphenylglycyl derivatives. In the test employing a dose of 100 mg/kg orally, BMY-28272 shows a greater AUC value, longer duration of blood levels, but somewhat shorter T1/2 than BMY-28100. In the test employing a dose of 20 mg/kg intramuscularly, BMY-28272 shows a greater AUC value and longer T1/2 than BMY-28100.

TABLE 3

Mouse Blood Levels

| | p.o. | | | | | i.m. | |
|---|---|---|---|---|---|---|---|
| | Dose: 100 mg/kg p.o. | | 20 mg/kg p.o.* | | | 20 mg/kg | |
| Time (hr) | BMY-28272 mcg/ml | BMY-28100 mcg/ml | BMY-28272 mcg/ml | BMY-28100 mcg/ml | Time (min) | BMY-28272 mcg/ml | BMY-28100 mcg/ml |
| 0.5 | 23 | 33 | 7.7 | 9.3 | 10 | 20 | 14 |
| 1.0 | 22 | 17 | 4.2 | 6.9 | 20 | 17 | 15 |
| 2.0 | 16 | 6.5 | 1.6 | 4.2 | 30 | 17 | 12 |
| 3.0 | 10 | 4.5 | 0.62 | 2.5 | 40 | 12 | 8.5 |
| 4.0 | 6.3 | 3.3 | 0.22 | 0.97 | 50 | 11 | 7.5 |
| 5.0 | 3.1 | 2.7 | 0.13 | 0.81 | 60 | 9.4 | 5.4 |
| 6.0 | 2.8 | 2.5 | 0.082 | 0.65 | 90 | 4.8 | 2.5 |
| 7.0 | 2.5 | 1.7 | — | 0.34 | 120 | 2.6 | 1.6 |
| T ½ (hr) | 1.7 | 2.1 | 0.86 | 1.4 | T ½ (hr) | 0.60 | 0.52 |
| AUC (mcg · hr/ml) | 71 | 51 | 9.7 | 20 | AUC (mcg · hr/ml) | 20 | 13 |

*The following were obtained by another experiment: C$_{max}$ (mcg/ml), 9.6; T ½ (hr), 1.0; AUC (mcg · hr/ml), 17 for BMY-28272 and C$_{max}$, 12; T ½, 2.3 and AUC, 24 for BMY-28100.

Table 4 shows the data of urinary recovery for mice. Although the total recovery ratio of BMY-28272 is smaller than those of BMY-28100 and cefaclor, the elevated value in the period of 6–24 hours suggests that the rate of excretion of BMY-28272 is slower than BMY-28100 and cefaclor.

TABLE 4

| Mouse Urinary Recovery Dose: 20 mg/kg, p.o. | | | | | |
|---|---|---|---|---|---|
| Compound | 0–2 hr | 2–4 hr | 4–6 hr | 6–24 hr | Total |
| BMY-28272 | 37% | 4.4% | 0.4% | 8.7% | 51% |
| BMY-28100 | 60% | 5.3% | 1.3% | 2.3% | 69% |
| Cefaclor | 60% | 6.7% | 0.3% | 1.5% | 69% |

Table 5 contains comparative data for in vitro antibacterial activity against fastidious bacteria. BMY-28272 shows the activity much better than cefaclor or cephalexin and is almost comparable or better than BMY-28100 against the fastidious bacteria.

TABLE 5

| In vitro Activity Against Fastidious Bacteria | | | | |
|---|---|---|---|---|
| | MIC (mcg/ml) | | | |
| Organism | BMY-28272 | BMY-28100 | Cefaclor | Cephalexin |
| [S. pyogenes] | | | | |
| S. pyogenes s-23 | 0.05 | 0.05 | 0.2 | 0.8 |
| S. pyogenes Dick | 0.05 | 0.05 | 0.2 | 0.8 |
| S. pyogenes A9604 | 0.05 | 0.05 | 0.2 | 0.8 |
| S. pyogenes A20065 | 0.05 | 0.05 | 0.2 | 0.8 |
| S. pyogenes A15040 | 0.05 | 0.05 | 0.2 | 0.8 |
| S. pyogenes A20201 | 0.05 | 0.05 | 0.2 | 0.8 |
| [S. pneumoniae] | | | | |
| S. pneumoniae Type II | 0.1 | 0.1 | 0.8 | 1.6 |
| S. pneumoniae Type I | 0.1 | 0.1 | 1.6 | 3.1 |
| S. pneumoniae Type III | 0.4 | 0.2 | 1.6 | 3.1 |
| S. pneumoniae A9585 | 0.1 | 0.1 | 0.8 | 1.6 |
| S. pneumoniae A15069 | 0.4 | 0.4 | 3.1 | 3.1 |
| S. pneumoniae A20759 | 0.4 | 0.4 | 3.1 | 3.1 |
| [N. gonorrheae] | | | | |
| N. gonorrheae A15112 | 0.4 | 0.8 | 0.8 | 6.3 |
| N. gonorrheae A20143 | 0.8 | 0.8 | 0.8 | 6.3 |
| N. gonorrheae A20154 | 0.8 | 0.8 | 0.8 | 6.3 |
| N. gonorrheae A20155 | 0.4 | 0.8 | 0.8 | 6.3 |
| N. gonorrheae A22442 | — | — | — | — |
| [N. meningitidis] | | | | |
| N. meningitidis A20048 | 0.8 | 0.4 | 0.8 | 3.1 |
| N. meningitidis A20049 | 0.8 | 0.4 | 0.8 | 3.1 |
| N. meningitidis A21487 | 0.8 | 0.4 | 0.8 | 3.1 |
| N. meningitidis A21495 | 0.4 | 0.4 | 0.8 | 3.1 |
| N. meningitidis A21497 | 0.4 | 0.4 | 0.8 | 3.1 |
| [H. influenzae; ABPC-S*] | | | | |
| H. influenzae A9729 | 0.4 | 0.8 | 0.8 | 3.1 |
| H. influenzae A20177 | 0.8 | 0.8 | 0.8 | 3.1 |
| H. influenzae A20193 | 0.8 | 0.8 | 0.8 | 3.1 |
| H. influenzae A21523 | 0.8 | 0.8 | 0.8 | 3.1 |
| H. influenzae A9833 | 0.4 | 0.8 | 0.8 | 3.1 |
| H. influenzae A22483 | 0.4 | 0.8 | 0.8 | 3.1 |
| H. influenzae A22482 | 0.4 | 0.8 | 0.8 | 3.1 |
| [H. influenzae; ABPC-R*] | | | | |
| H. influenzae A22157 | 0.4 | 0.8 | 1.6 | 3.1 |
| H. influenzae A22481 | 0.8 | 0.8 | 1.6 | 3.1 |
| H. influenzae A22491 | 0.8 | 0.8 | 1.6 | 3.1 |

*ABPC-S = Ampicillin-sensitive; ABPC-R = Ampicillin-resistant

The compound of the present invention is prepared by application of the synthesis routes disclosed in U.S. Pat. No. 4,520,022. The most typical preparation procedures are illustrated in Scheme 1.

The amino group of DL-3-hydroxyphenylglycine (1) is protected with t-butoxycarbonyl by using di-tert-butyl dicarbonate to give DL-N-tert-butoxycarbonyl-3-hydroxyphenylglycine (2). In this case, D-3-hydroxyphenylglycine may be used instead of the racemic phenylglycine. The resulting N-protected phenylglycine (2) is coupled with benzhydryl 7-amino-3-[(Z)-1-propenyl]-3-cephem-4carboxylate (3) to afford benzhydryl 7-[DL-2-N-tert-butoxycarbonylamino-2-(3-hydroxyphenyl)acetamido]-3-[(Z)-1-propenyl]-3-cephem-4-carboxylate (4). Deblocking and chromatographical separation (reverse phase chromatography) gives the desired 7-[D-2-amino-2-(3-hydroxyphenyl)acetamido]-3-[(Z)-1-propenyl]-3-cephem-4-carboxylic acid (I, BMY-28272). Another typical procedure is to apply the Wittig reaction to build the propenyl part at the 3-position of the cephem nucleus after the 7-acylation. The N-protected D-phenylglycine (2) is coupled with benzhydryl 7-amino-3-chloromethyl-3-cephem-4-carboxylate (5) to furnish benzhydryl 7-[D-2-N-tert-butoxycarbonylamino-2-(3-hydroxyphenyl)acetamido[-3-chloromethyl-3-cephem-4-carboxylate (6). The compound (6) is treated with NaI and then reacted with triphenylphosphine to give the triphenylphosphonium salt (7). The phosphonium salt is converted to the phosphoranyl intermediate by treating with sodium hydroxide. This phosphoranyl intermediate is then reacted with acetaldehyde to give the desired 3-propenylcephalosporin intermediate (4).

Scheme 1
Preparation of BMY-28272

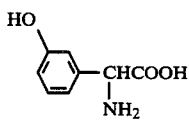

1

-continued
Scheme 1
Preparation of BMY-28272

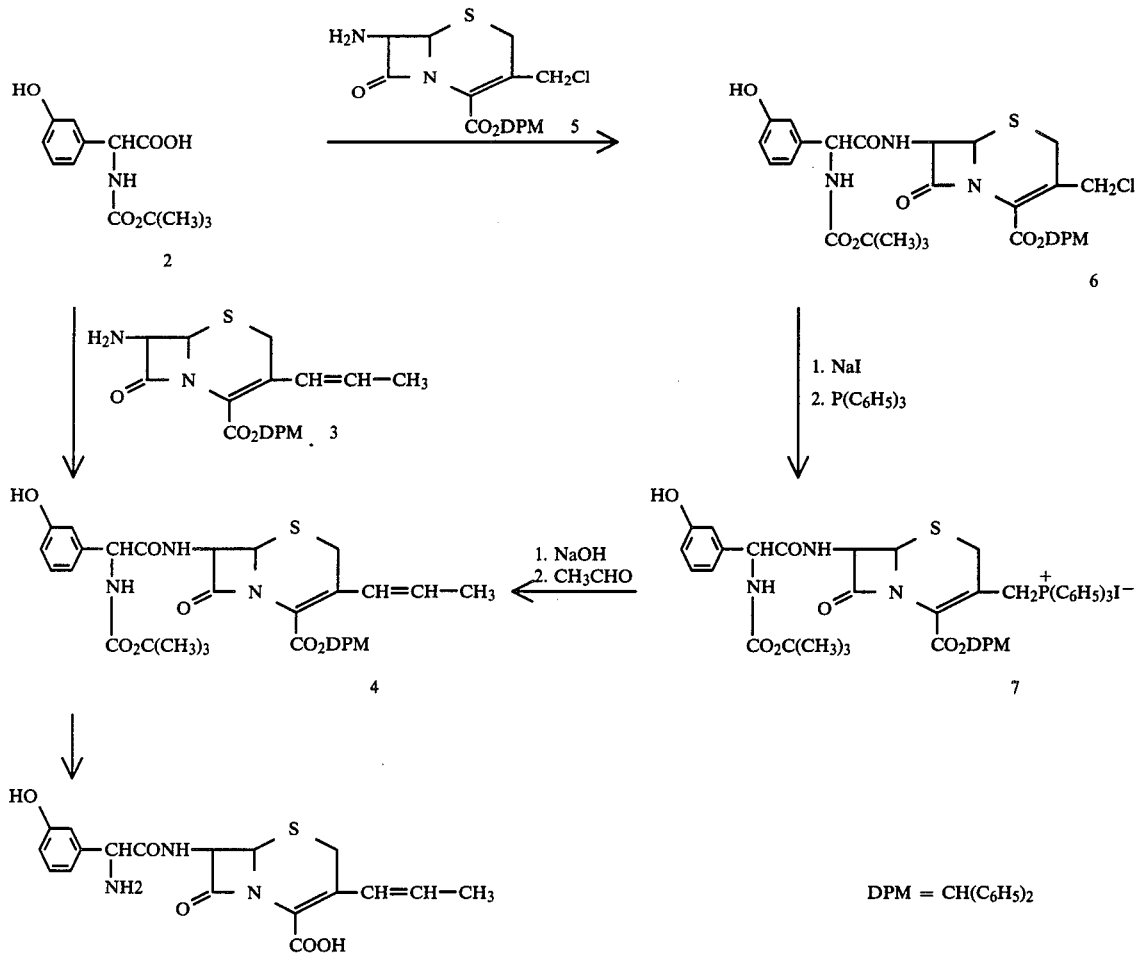

I, BMY-28272

DPM = CH(C₆H₅)₂

EXAMPLE 1

DL-2-N-tert-Butoxycarbonylamino-2-(3-hydroxyphenyl)acetic acid (2)

To a mixture of DL-2-(3-hydroxyphenyl)glycine (1) (2 g, 0.012 mole) and di-tert-butyl dicarbonate (2.6 g, 0.012 mole) in a 50% aqueous tetrahydrofuran (THF, 40 ml) was added triethylamine (3.4 ml, 0.024 mole), and the mixture was stirred at room temperature for 5 hours, concentrated to ca. 20 ml, washed with ether (50 ml), acidified with 40% phosphoric acid and extracted with ether (100 ml×2). The combined extracts were washed with water and a saturated aqueous NaCl solution successively, dried with MgSO₄, treated with active-carbon and evaporated to afford an oil. The oily residue was triturated with n-hexane to give 2.7 g (84%) of the title compound. Mp. 144°–148° C. (dec).

IR: $\nu_{max}$ (KBr) in cm$^{-1}$ 1760, 1630, 1590, 1560, 1370, 1340, 1290, 1250, 1210, 1160.

UV: $\lambda_{max}$ (CH₃OH) in nm ($\epsilon$) 276 (2300), 282 (2000).
NMR: δ(CDCl₃+DMSO) in ppm 1.42 (9H, s, C-CH₃), 5.13 (1H, d, J=7 Hz, CH-NH), 5.82 (1H, d, J=7 Hz, NH-CH), 6.8–7.3 (4H, m, phenyl-H).

Anal. Calc'd. for C₁₃H₁₇NO₅: C, 58.42; H, 6.41; N, 5.24. Found: C, 58.73; H, 6.70; N, 5.17.

EXAMPLE 2

Benzhydryl 7-[2-N-tert-butoxycarbonylamino-2-(3-hydroxyphenyl)-acetamido]-3-[(Z)-1-propenyl]-3-cephem-4-carboxylate [(4), a mixture of the diastereoisomers]

A suspension of benzhydryl 7-amino-3-[(Z)-1-propenyl]-3-cephem-4-carboxylate hydrochloride (3) (443 mg, 1 mmole) in a mixture of ethyl acetate-THF (10:1, 55 ml) was vigorously shaken with an aqueous NaHCO₃ solution (50 ml). The organic layer was taken up, washed with water and a saturated NaCl solution successively, dried with MgSO₄ and concentrated to ca. 30 ml. To the concentrate were added DL-2-N-tert-butoxycarbonylamino-2-(3-hydroxyphenyl)acetic acid (2) (320 mg, 1.2 mmoles) and N,N'-dicyclohexylcarbodiimide (250 mg, 1.2 mmoles). The mixture was stirred at room temperature for 0.5 hour and filtered, and the filtrate was evaporated to dryness to give a residue which was purified by column chromatography (Kiesel gel 60, Merck, 30 g) by eluting with toluene-ethyl acetate (4:1). The desired fractions, monitored by TLC, were collected and evaporated to dryness. The residue was triturated with ether-isopropyl ether-n-hexane to give 627 mg (95%) of solid as a mixture of the diastereoisomers. Mp. 120° C. (dec.).

IR: $\nu_{max}$ (KBr) in cm$^{-1}$ 1780, 1710, 1690, 1590, 1500, 1370, 1220, 1160.

UV: $\lambda_{max}$ (CH$_3$OH) in nm ($\epsilon$) 283 (9900).

EXAMPLE 3

BMY-28272;
7-[D-2-Amino-2-(3-hydroxyphenyl)acetamido]-3-[(Z)-1-propenyl]-3-cephem-4-carboxylic acid (I)

A mixture of benzhydryl 7-[DL-2-N-tert-butoxycarbonylamino-2-(3-hydroxyphenyl)acetamido]-3-[(Z)-1-propenyl]-3-cephem-4-carboxylate (4) (600 mg, 0.91 mmole), anisole (0.5 ml) and trifluoroacetic acid (TFA, 2 ml) was stirred at room temperature for 10 minutes, and the mixture was diluted with 50 ml of etherisopropyl ether (1:1). The resulting precipitate was collected by filtration to give 438 mg (95%) of the crude product of I (a mixture of the diastereoisomers), which was chromatographed on a column packed with the packing of prepPAK-C$_{18}$ cartridge (Waters) by eluting with water, 5% methanol and 10% methanol, successively. The eluates were monitored by HPLC and the fraction eluted with 5% methanol was concentrated. The residue (153 mg) was chromatographed again on a 300 ml column by eluting with 10% methanol to give 57 mg of the crude D isomer. The fraction eluted with 10% methanol was collected, concentrated to ca. 10 ml and lyophilized to give 83 mg of another crude D isomer. Both crude products (ca. 140 mg) were combined and chromatographed on a 300 ml column, which was eluted with 10% and 20% methanol successively to afford the title compound (106 mg, 30%). Purity 90% by HPLC (25% methanol-buffer, retention time, 10.24 minutes). Mp. 200° C. (grad. dec.).

IR: $\nu_{max}$ (KBr) in cm$^{-1}$ 1750, 1680, 1580, 1390, 1350, 1280.

UV: $\lambda_{max}$ (pH 7 buffer) in nm ($\epsilon$) 280 (10000).

NMR: $\delta$(D$_2$O+Na$_2$CO$_3$) in ppm 1.42 (3H, d-d, J=6 and 1.5 Hz, =CH—CH$_3$), 3.02 (1H, d, J=18 Hz, 2-H), 3.27 (1H, d, J=18 Hz, 2-H), 4.57 (1H, s, CH—CO), 4.93 (1H, d, J=4.5 Hz, 6-H), 5.48 (1H, d, J=4.5 Hz, 7-H), 5.4–5.6 (1H, m, CH=C), 5.68 (1H, d-d, J=11 and 1.5 Hz, CH=C), 6.7–6.9 (3H, m, phenyl-H), 7.1–7.2 (1H, m, phenyl-H).

EXAMPLE 4

Benzhydryl
7$\beta$-[D-2-(t-butoxycarbonylamino)-2-(3-hydroxyphenyl)-acetamido]-3-chloromethyl-3-cephem-4-carboxylate (6)

To a mixture of 20.7 g (0.05 mole) of benzhydryl 7-amino-3-chloromethyl-3-cephem-4-carboxylate (5) and 20 g (0.075 mole) of D-2-(t-butoxycarbonylamino)-2-(3-hydroxyphenyl)acetic acid (2) in 500 ml of dry tetrahydrofuran (THF) was added 15.45 g (0.075 mole) of N,N'-dicyclohexylcarbodiimide (DCC), and the mixture was stirred at room temperature for 2 hours and evaporated to dryness. The residue was dissolved in 1 L of ethyl acetate (AcOEt), and the insoluble dicyclohexylurea was removed by filtration. The filtrate was washed with an aqueous sodium bicarbonate solution, water and saturated aqueous NaCl solution, dried on anhydrous sodium sulfate and evaporated to dryness. The oily residue was chromatographed on a column of silica gel (Wako gel C-100, 500 g) by eluting with 4 liters of chloroform and 6 liters of 1% chloroform-methanol. The desired fractions were combined and evaporated to dryness. The oily residue was triturated with ether-isopropyl ether to give 31 g (90%) of the title compound.

IR: $\nu_{max}$ (KBr, cm$^{-1}$) 1790, 1710, 1670, 1230, 1150.

EXAMPLE 5

Benzhydryl
7$\beta$-[D-2-(t-butoxycarbonylamino)-2-(3hydroxyphenyl)-acetamido]-3-(triphenylphosphonio)methyl-3-cephem-4-carboxylate iodide (7)

A mixture of 26.6 g (0.04 mole) of (6) and 18 g (0.12 mole) of sodium iodide in 400 ml of acetone was stirred at room temperature for 2 hours and evaporated to dryness. The residue was extracted with 400 ml of ethyl acetate, and the extract was washed with an aqueous Na$_2$S$_2$O$_3$ solution, water and a saturated aqueous NaCl solution. After evaporation of the solvent, the residue was triturated with ether-isopropyl ether to give 27 g of solid. A mixture of 15.1 g of the solid and 15.7 of triphenylphosphine in 200 ml of ethyl acetate was stirred at room temperature for one hour. The resulting precipitate was collected by filtration to give 17.4 g (77%) of the tite compound.

IR: $\nu_{max}$ (KBr, cm$^{-1}$) 1780, 1670, 1490, 1420, 1350, 1240, 1150, 1090.

EXAMPLE 6

Benzhydryl
7$\beta$-]D-2-(t-butoxycarbonylamino)-2-(3-hydroxyphenyl)-acetamido]-3-[(Z)-1-propen-1-yl]ceph-3-em-4-carboxylate [(4), D-isomer]

To a solution of 1.8 g (1.77 mmol) of (7) in 100 ml of chloroform was added 100 ml of water containing 2 ml (2 mmoles) of N sodium hydroxide, and the mixture was shaken for 5 minutes. The organic layer was separated, washed with water and dried on anhydrous sodium sulfate. The chloroform solution being filtered, the filtrate was concentrated to 50 ml under reduced pressure. To the concentrate was added 1 g of acetaldehyde, and the mixture was stirred at room temperature for 2 hours and evaporated to dryness. The oily residue was chromatographed on a silica gel column (Wako gel C-200, 50 g) by eluting with chloroform and chloroform-methanol (99:1). The desired fractions were collected and evaporated to give 318 mg (28%) of the title compound, mp. 120° C. (dec.).

IR: $\nu_{max}$ (KBr, cm$^{-1}$) 1780, 1710, 1500, 1220.

EXAMPLE 7

BMY-28272:
7$\beta$-[D-2-Amino-2-(3-hydroxyphenyl)acetamido]-3-[(Z)-1-propen-1-yl]-3-cephem-4-carboxylic acid (I)

A mixture of 318 mg (0.48 mmole) of (4) in Example 6, and 2.5 ml of trifluoroacetic acid (TFA) was stirred at room temperature for one hour and then diluted with 50 ml of ether and 50 ml of isopropyl ether. The precipitate which separated was collected and chromatographed on a column packed with the packing of prepPAK-C$_{18}$ cartridge (Waters) by eluting with 5% methanol. The desired fractions were collected and evaporated to give 150 mg of the title compound. Physico-chemical data for this material were identical to those of the compound obtained in Example 3.

Waht is claimed is:

1. 7β-[D-2-Amino-2-(3-hydroxyphenyl)acetamido]-3-[(Z)-1-propen-1-yl]-3-cephem-4-carboxylic acid and the pharmaceutically acceptable esters, acid addition, and metal salts thereof, said salts being antibacterially effective on oral or parenteral administration.

2. The compound of claim 1 having the chemical name 7β-[D-2-amino-2-(3-hydroxyphenyl)acetamido]-3-[(Z)-1-propen-1-yl]-3-cephem-4-carboxylic acid.

3. A method for the treatment of a bacterial infection in a mammal caused by an organism sensitive to a substance claimed in claim 1 which comprises administering an antibacterially effective non-toxic dose of one of said substances to the infected mammal on a repetitive dosage regimen for a treatment period of sufficient duration to mitigate said infection.

4. A pharmaceutical composition in unit dosage form containing an antibacterially effective non-toxic amount of a compound claimed in claim 1 and a pharmaceutically acceptable carrier therefor.

* * * * *